(12) United States Patent
Mukherjee et al.

(10) Patent No.: US 9,662,059 B2
(45) Date of Patent: May 30, 2017

(54) IMAGING AGENTS FOR MONITORING CHANGES OF DOPAMINE RECEPTORS AND METHODS OF USING THEREOF

(75) Inventors: Jogeshwar Mukherjee, Irvine, CA (US); George Chandy, Laguna Beach, CA (US); Norah Milne, Mission Viejo, CA (US); Ping H. Wang, Irvine, CA (US); Balu Easwaramoorthy, New York, NY (US); Joseph Mantil, Dayton, OH (US); Adriana Garcia, Newport Beach, CA (US)

(73) Assignee: The Regents of the University of California, Oakland, CA (US)

(*) Notice: Subject to any disclaimer, the term of this patent is extended or adjusted under 35 U.S.C. 154(b) by 1183 days.

(21) Appl. No.: 12/110,135

(22) Filed: Apr. 25, 2008

(65) Prior Publication Data

US 2008/0319310 A1 Dec. 25, 2008

Related U.S. Application Data

(60) Provisional application No. 60/926,564, filed on Apr. 26, 2007.

(51) Int. Cl.
| | |
|---|---|
| *A61B 6/00* | (2006.01) |
| *A61B 5/00* | (2006.01) |
| *A61B 5/145* | (2006.01) |
| *A61B 6/03* | (2006.01) |
| *A61B 5/055* | (2006.01) |

(52) U.S. Cl.
CPC .......... *A61B 5/417* (2013.01); *A61B 5/14532* (2013.01); *A61B 6/037* (2013.01); *A61B 5/055* (2013.01)

(58) Field of Classification Search
None
See application file for complete search history.

(56) References Cited

U.S. PATENT DOCUMENTS

2005/0065078 A1* 3/2005 Cawthorne ............ A23C 9/152
514/5.3

OTHER PUBLICATIONS

Mukherjee et al, "Brain Imaging of 18F-Fallypride in Normal Volunteers: Blood Analysis, Distribution, Test-Retest Studies, and Preliminary Assessment of Sensitivity to Aging Effects on Dopamine D-2/D-3 Receptors", Synapse 46: 170-188 (2002).*
Rubi et al, "Dopamine D2-like Receptors Are Expressed in Pancreatic Beta Cells and Mediate Inhibition of Insulin Secretion", The Journal of Biological Chemistry, vol. 280, No. 44, pp. 36824-36832, Nov. 4, 2005.*
Chan et al., Reproducability of Repeated Measures of Cholinergic Terminal Density Using [18F](+)-4-Fluorobenzyltrozamicol and PET in the Phesus Monkey Brain, The Journal of Nuclear Medicine (Dec. 1, 2000), pp. 2069-2076, 41(12).

(Continued)

*Primary Examiner* — Katherine Fernandez
*Assistant Examiner* — Farshad Negarestan
(74) *Attorney, Agent, or Firm* — Archer Norris, PLC; Sean D. Senn; Priti D. Phukan

(57) ABSTRACT

The present invention is related generally to a method for screening subjects to determine those subjects more likely to develop diabetes by quantization of insulin producing cells. The present invention is also related to the diagnosis of diabetes and related to monitor disease progression or treatment efficacy of candidate drugs.

10 Claims, 8 Drawing Sheets

(56) References Cited

OTHER PUBLICATIONS

Denis et al., Imaging Inflammation of the Pantreatic Isletes in Type I Diabetes, Proceedings of the National Academy of Sciences USA (Aug. 24, 2004), pp. 12634-12639, 101(34).

Hardy et al., Diagnosis and Localization of Focal Congenital Hyperinsulinism by 18F-Fluorodopa PET Scan, Journal of Pediatrics (Feb. 2007), pp. 140-145, 150(2).

Kauhanen et al., Fluorine-18-L-Dihydroxyphenylalanine (18F-DOPA) Positron Emission Tomography as a Tool to Localize an Insulinoma or β-Cell Hyperplasia in Adult Patients, The Journal of Clinical Endocrinology & Metabolism (Apr. 2007), pp. 1234-1244, 92(4).

Mukherjee et al., 11C-Fallypride: Radiosynthesis and Preliminary Evaluation of a Novel Dopamine D2/D3 Receptor PET Radiotracer in Non-Human Primate Brain, Bioorganic & Medicinal Chemistry (Jan. 2, 2004), pp. 95-102, 12(1).

Mukherjee et al., Preliminary Assessment of Extrastriatal Dopamine D-2 Receptor Binding in the Rodent and Nonhuman Primate Brains Using the High Affinity Radioligand, 18F-fallypride, Nuclear Medicine and Biology (Jul. 1999), pp. 519-527, 26(5).

Mukherjee et al., Fluorinated Benzamide Neuroleptics—III. Development of (S)-N-[(1-allyl-2-pyrrolindinyl)methyl]-5-(3-[18F]fluoropropul)-2,3-dimethoxybenzamide as an Improved Dopamine D-2 Receptor Tracer, Nuclear Medicine and Biology (Apr. 1995), pp. 283-296, 22(3).

Shankar et al., Dopaminergic Regulation of Clucose-Induced Insulin Secretion Through Dopamine D2 Receptors in the Pancreatic Islets in Vitro, IUBMB Life (Mar. 2006), pp. 157-163, 58(3).

Simpson et al., Author Manuscript of: Visualizing Pancreatic β-Cell Mass With [11C]DTBZ, available through NIH Public Access, Published in Final Edited Form in Nuclear Medicine and Biology (Oct. 2006), pp. 855-865, 33(7).

Souza et al., Current Progress in Non-Invasive Imaging of Beta Cell Mass of the Endocrine Pancreas, Current Medicinal Chemistry (2006), pp. 2761-2773, 13(23).

Souza et al., Longitudinal Noninvasive PET-Based β-Cell Mass Estimates in a Spontaneous Diabetes Rat Model, Journal of Clinical Investigation (Jun. 2006), 116(6).

Sperling, M., PET Scanning for Infants with HHI: A Small Step for Affected Infants, a Giant Leap for the Field, The Journal of Pediatrics (Feb. 2007), pp. 122-124, 150(2).

Sweet et al., Systematic Screening of Potential β-Cell Imaging Agents, Biochemical and Biophysical Research Communications (Feb. 20, 2004), pp. 976-983, 314(4).

Christian, B.T. et al, Quantitation of Striatal and Extrastriatal D-2 Dopamine Receptors Using PET Imaging of [18F] Fallypride in Nonhuman Primates, Synapse, 2000, pp. 71-79, 38(1).

Mukherjee, J. et al, Evaluation of Dopamine D-2 Receptor Occupancy by Clozapine, Risperidone, and Haloperidol In Vivo in the Rodent and Nonhuman Primate Brain Using 18F-Fallypride, Neuropsychopharmacology, 2001, pp. 476-488, 25(4).

Narayanan, T.K. et al, A Comparative Study on the Uptake and Incorporation of Radiolabeled Methionine, Choline and Fluorodeoxyglucose in Human Astrocytoma, Molecular and Imaging Biology, 2002, pp. 147-156, 4(2).

Chattopadhyay, S., et al. Synthesis and Evaluation of Nicotine α4β2 Receptor Radioligand, 5-(3'-18F-Fluoropropyl)-3-(2-(S)-Pyrrolidinylmethoxy) Pyridine, in Rodents and PET in Nonhuman Primate, Journal of Nuclear Medicine, 2005, pp. 130-140, 46(1).

Adriana Garcia, et al.; 18F-Fallypride PET of Pancreatic Islets Cells: In Vitro and In Vivo Rodent Studies; The Journal of Nuclear Medicine, vol. 52, No. 7 1125-1132; Jul. 2011.

Adriana Garcia, et al.; Imaging Pancreas in Healthy and Diabetic Rodent Model Using 18F-Fallypride Positron Emission Tomography/Computed Tomography; Diabetes Technology & Therapeutics, vol. 16, No. 10: 640-643; 2014.

\* cited by examiner

1L  X = F, R = CH$_3$          Fallypride
1b  X = $^{18}$F, R = CH$_3$    $^{18}$F-Fallypride
1c. X = F, R = $^{11}$CH$_3$    $^{11}$C-Fallypride

IMAGING AGENTS FOR MONITORING CHANGES OF DOPAMINE RECEPTORS AND METHODS OF USING THEREOF

RELATED APPLICATION

This application claims priority to U.S. Provisional Application No. 60/926,564 filed Apr. 26, 2007, the contents of which is hereby incorporated in its entirety by reference.

GOVERNMENT RIGHTS

This invention was made with government support under Grant Nos. DE-FG02-03ER63598, awarded by the U.S. Department of Energy. The Government has certain rights in this invention.

TECHNICAL FIELD

The present invention is related generally to a method for screening subjects to determine those subjects more likely to develop diabetes by quantization of insulin producing cells. The present invention is also related to the diagnosis of diabetes and related to monitor disease progression or treatment efficacy of candidate drugs.

BACKGROUND OF THE INVENTION

Loss of insulin producing cells in the pancreatic islets, the endocrine component of pancreas, referred here as beta cell mass (BCM), leads to an inability to manage blood sugar levels. This results in diabetes mellitus, type 1 (T1DM) or type 2 (T2DM). T1DM, has previously been known as "insulin-dependent diabetes mellitus," (IDDM) or "juvenile diabetes." T1DM is a life-long condition in which the pancreas stops making insulin due to loss of BCM from an autoimmune response. Without insulin, the body is not able to use blood sugar for energy. T1DM treatment involves insulin injections, following a diet plan and exercise, and test blood sugar several times a day. T1DM usually begins before the age of 30. T2DM, previously known as "noninsulin-dependent diabetes mellitus" (NIDDM) or "adult-onset diabetes", is the most common form of diabetes. About 90 to 95 percent of people who have diabetes have T2DM. People with T2DM diabetes produce insulin, but either do not make enough insulin or their bodies do not use the insulin they make. Individuals with T2DM are overweight and may be able to control their condition by losing weight through diet and exercise and may also need to inject insulin or take medicine along with continuing to follow a healthy program of diet and exercise. Although T2DM commonly occurs in adults, an increasing number of children and adolescents who are overweight are also developing T2DM.

Despite rigorous control of blood sugar, the majority of diabetic patients develop serious late-stage complications including retinopathy, nephropathy, neuropathy, microangiopathy and strokes. A long asymptomatic preclinical period characterized by gradual BCM loss precedes clinical T1DM. The duration of the preclinical phase varies substantially because the disease can be diagnosed both in infancy and in older age groups. The highest incidence is reported in children, with an obvious peak in early puberty. Methods to predict the development of clinical T1DM currently rely on the detection of multiple autoantibodies to islet-associated proteins combined with HLA genotyping. Improvement of the power and reliability of methods to predict diabetes would raise the possibility for pharmacological intervention during the preclinical phase and the honeymoon period to either slow down or arrest the ongoing destruction of the remaining β-cells. Currently, the only accepted end-point for drug trials is the clinical diagnosis of T1DM. Despite rigorous control of blood sugar, the majority of diabetic patients develop serious late-stage complications including retinopathy, nephropathy, neuropathy, microangiopathy and strokes. A long asymptomatic preclinical period characterized by gradual BCM loss precedes clinical T1DM. The duration of the preclinical phase varies substantially because the disease can be diagnosed both in infancy and in older age groups. The highest incidence is reported in children, with an obvious peak in early puberty. Methods to predict the development of clinical T1DM currently rely on the detection of multiple autoantibodies to islet-associated proteins combined with HLA genotyping. Improvement of the power and reliability of methods to predict diabetes would raise the possibility for pharmacological intervention during the preclinical phase and the honeymoon period to either slow down or arrest the ongoing destruction of the remaining β-cells. Currently, the only accepted end-point for drug trials is the clinical diagnosis of T1DM.

A non-invasive imaging approach to monitor BCM would enable earlier and better diagnosis/management of both T1DM and T2DM since pancreas is not an ideal organ for biopsy. Several groups have described non-invasive imaging approaches to detect and follow loss of BCM and has been reviewed recently (Souza et al., Cur Med Chem 2006 13:2761). Each of these methods has advantages and disadvantages. For example, bioluminescence imaging using luciferase-expressing mouse or human islets restored euglycemia in NOD-SCID mice and the bioluminescence of the transplanted islets was quantified with a high degree of sensitivity. An early MRI approach tracked the ingress into islets of adoptively transferred lymphocytes pre-labeled with superparamagnetic iron oxide particles (CLIO) and FITC-conjugated Tat-derived peptide. Ex vivo MRI imaging detected the labeled lymphocytes in the islets of NOD-SCID mice but not control C57BL/6J mice. An extension of this method involved pre-labeling $CD8^+$ lymphocytes with nanoparticles of CLIO-NOD-relevant V7 (CLIO-NRP-V7) peptide and transferring them into 8.3-NOD mice, which express a transgenic T cell receptor that recognizes NRP-V7. In vivo MRI imaging detected islet infiltration of the transferred lymphocytes. This MRI method requires pre-labeling of lymphocytes before transfer into recipients, which is a limitation when studying the progression of insulitis and β-cell loss during T1DM. A magnetic resonance imaging (MRI) approach involves the visualization of pancreatic microvasculature changes that accompany insulitis. Injected monocrystalline dextran-coated iron oxide superparamagnetic nanoparticles exit the blood stream at sites of vascular leakage. In NOD mice, MRI revealed accumulation of the magnetic particles in macrophages that infiltrated islets during EAD. Translation of this promising technique into the clinical realm could provide a vital tool for the early detection of insulitis and 1-cell destruction.

Various radiotracer methods are currently underway to study differential pancreatic uptake of 6-deoxy-6-$^{125}$I-iodo-D-glucose, $^3$H-monosaccharide D-mannoheptulose, $^3$H-glibenclamide, 2-$^{14}$C-alloxan, $^{11}$C-acetate and $^{11}$C-methionine have been reported. Ex vivo radioimmunoscintigraphy with radio-labeled anti-IC2 monoclonal antibody showed a significant reduction in β-cells in streptozotocin-induced diabetes, but the method has yet to be used in vivo. In a recent PET study, VMAT2 (vesicular monoamine transporter-2) in pancreatic beta cells and in sympathetic nerve terminals that innervate islets and exocrine pancreas, was targeted using the specific radioligand $^{11}$C-dihydrotetrabenazine. Serial PET scanning over a 5 week period revealed a 50% loss in β-cell mass that accompanied the progression of EAD in DP-BB/W rats (Souza et al., J Clin Invest 2006 116:1506; Simpson et al., Nucl Med Biol 2006 33:855). Another recent promising study is the use of $^{18}$F-FDOPA which was successfully used to diagnose infants with congenital hyperinsulinism (Hardy et al., J Pediatrics 2007 150:140). This ability to diagnose insulin-related disorders is in great need (Sperling J Pediatrics 2007 150:122).

Dopamine D2 receptor (D2R) expression have recently been demonstrated on rodent and human β-cells using isolated islets and beta cell lines (Rubi et al., J Biol Chem 2005 280:36824). D2Rs co-localized with insulin in intracellular granules and quinpirole, a D2R agonist, inhibited glucose-dependent insulin secretion. This report did not ascertain if D2R expression in the pancreas was confined to the endocrine pancreatic islets, or whether it was also present in the exocrine tissues.

We have been involved in developing noninvasive PET diagnostic imaging methods for D2R. A novel dopamine D2/D3 receptor imaging agent fallypride (FIG. 1, labeled with either carbon-11 (20 min half-life) or fluorine-18 (110 min half-life)) has been developed and we have shown its ability to study both the human and nonhuman brain and other peripheral organs (Mukherjee et al., Nucl Med Biol 1995 22:283; Mukherjee et al., Nucl Med Biol 1999 26:519; Mukherjee et al. Synapse 2002 46:170; Mukherjee et al. Bioorganic Medicinal Chem 2004 12:95; Xue et al., J Nucl Med 2004 45:258P).

In one aspect, this application provides novel diagnostic markers for BCM and therefore be useful for evaluating T1DM, T2DM and related disorders of the pancreas or identifying individuals or patients who will develop T1DM, T2DM in the near future.

SUMMARY OF THE INVENTION

The present application provides a non-invasive method of monitoring changes in beta cell mass in a subject comprising detecting a level of Dopamine receptor in the pancreas of said subject. The application also provides a non-invasive method of determining whether a subject is developing diabetes comprising detecting a level of Dopamine receptor in the pancreas of said subject.

In one embodiment of any of the aspects disclosed herein, the Dopamine receptor is optionally a D2 or D2-like receptor. In one embodiment the detecting step can include
a) administering an imaging agent comprising said Dopamine receptor into said subject; and
b) measuring imaging signals of said imaging agent in the pancreas of said subject. The imaging agent can be a positron emitting imaging agent and or a radiolabelled compound. For example, the imaging agent can be $^{18}$F-fallypride, $^{18}$F-desmethoxyfallypride, $^{11}$C-fallypride, $^{11}$C-desmethoxyfallypride, $^{11}$C-raclopride, or $^{11}$C-FLB457. The imaging agent can be a photon emitting imaging agent.

The imaging signal of the imaging agent can be measured by positron emission tomography (PET), positron emission tomography-computerized tomography (PET/CT) or positron emission tomography-magnetic resonance imaging (PET/MRI). The imaging signal can also be measured by single photo emission computed tomography (SPECT). For example, the imaging agent can be $^{123}$I-IBZM, $^{123}$I-epidepride, or $^{123}$I-IBF (iodo-benzofuran). The imaging signal can be measured by single photo emission computed tomography (SPECT) in combination with MRI or CT.

In a related aspect, the present application discloses methods of monitoring disease progression of a subject developing diabetes. The method includes 1) detecting a level of Dopamine D2 receptor in the pancreas of said subject at a first and a second time point; 2) comparing the detected levels between the first and second time points; and 3) determining the disease progression of said subject. The subject is making a progression toward diabetes if the levels at first time point is high than the level at second time point.

In another related aspect, the present application discloses methods of evaluating the therapeutic efficacy of a candidate drug in the prevention or treatment of diabetes when administered into a subject. The methods include 1) measuring level of Dopamine D2 receptor in the pancreas of said subject prior to and after administering said candidate drug into said subject; 2) comparing the measured Dopamine D2 receptor levels between prior to and after administering said candidate drug; and 3) determining therapeutic efficacy of a candidate drug, wherein the amount of increased Dopamine D2 receptor level is an indicator of therapeutic efficacy.

In yet another related aspect, the present application discloses a method of managing insulin dosage administered to a subject suffering from diabetes. The method includes 1) monitoring level of Dopamine D2 receptor in the pancreas of said subject after administration of insulin; 2) detecting loss of beta cell mass of said subject indicated by said level of Dopamine D2 receptor; and 3) modulating said insulin dosage so that beta cell mass is restored to normal.

In any of the methods disclosed herein, the patient can be at a clinical or preclinical stage of diabetes, e.g., Type I or Type II diabetes. Alternately, the patient can be at a preclinical or clinical stage of a diabetes-related metabolic syndrome.

In any of the methods disclosed herein, the imaging agent can be administered with glucose. For example, the imaging agent can be administered in an intravenous formulation comprising glucose. In another alternative, the imaging agent is contained in a solution comprising the imaging agent, glucose and a pharmaceutically acceptable excipient, such as for example, saline. Other appropriate pharmaceutically acceptable excipients are well known to those of skill in the art. In one alternative, the imaging agent is $^8$F-fallypride, $^{18}$F-desmethoxyfallypride, $^{11}$C-fallypride, $^{11}$C-desmethoxyfallypride, $^{11}$C-raclopride, or $^{11}$C-FLB457. In another alternative, the imaging agent is $^{18}$F-fallypride. Alternately, the imaging agent can be administered either concurrent with or sequential to administration of a formulation of intravenous glucose. With such an administration of an intravenous glucose formulation, diabetes imaging can take place along with or analogous to an intravenous glucose tolerance test. Alternately any of the methods disclosed herein can be conducted concurrent with or sequential to an oral glucose tolerance test. Administration of an oral glucose tolerance test is well-known to those of skill in the art.

In yet another related aspect, the present application discloses a non-invasive method of determining whether a subject is developing one or more islet cell disorder. The method includes detecting a level of Dopamine receptor in the pancreas of said subject, wherein said level of Dopamine receptor indicates density of beta cell mass of said subject. The islet cell disorder can be, e.g., insulinoma, islet cell hyperplasia, glucaginoma, or somastatinoma.

In another aspect, a non-invasive method of determining whether a subject is developing one or more glucose regulatory disorder is provided. The method includes detecting a level of Dopamine receptor in the pancreas of said subject, wherein said level of Dopamine receptor indicates density of beta cell mass of said subject.

These and other aspects of the invention will become more evident upon reference to the following detailed description and attached drawings. It is to be understood however that various changes, alterations and substitutions may be made to the specific embodiments disclosed herein without departing from their essential spirit and scope. In addition, it is further understood that the drawings are intended to be illustrative and symbolic representations of an exemplary embodiment of the present invention and that other non-illustrated embodiments are within the scope of the invention.

DETAILED DESCRIPTION OF THE INVENTION

Figure 1:
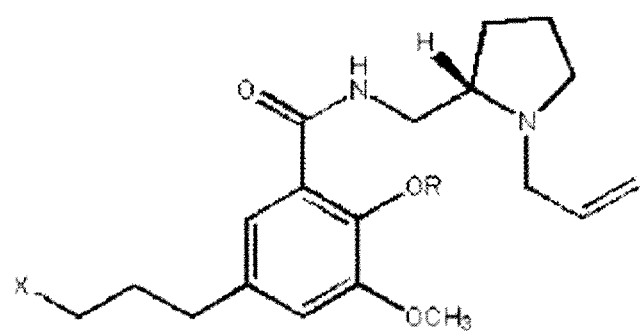
FIG. 1 is the chemical structure of fallypride, $^{18}$F-fallypride and $^{11}$C-fallypride.

Unless defined otherwise, technical and scientific terms used herein have the same meaning as commonly understood by one of skill in the art to which this invention belongs.

One skilled in the art will recognize many methods and materials similar or equivalent to those described herein, which could be used in the practice of this invention. Indeed the present invention is no way limited to the methods and materials described herein. For purposes of the present invention the following terms are defined.

I. DEFINITIONS

As used herein, the term "hyperglycemic disorders" refers to all forms of diabetes, such as type I and type II diabetes, as well as hyperinsulinemia and hyperlipidemia, e.g., obese subjects, and insulin-resistant diabetes, such as Mendenhall's Syndrome, Werner Syndrome, leprechaunism, lipoatrophic diabetes, and other lipoatrophies. Generally, the hyperglycemic disorder is diabetes, especially type I and type II diabetes. "Diabetes" itself refers to a progressive disease of carbohydrate metabolism involving inadequate production or utilization of insulin and is characterized by hyperglycemia and glycosuria. The criteria for the varying degrees of impairment in glucose tolerance are given in Table A. These criteria are used for the diagnosis of diabetes mellitus.

As used herein, the term "treating" is intended to mean an amelioration of a clinical symptom indicative of diabetes. Amelioration of a clinical symptom includes, for example, a decrease in blood glucose levels or an increase in the rate of glucose clearance from the blood in the treated individual compared to pretreatment levels or to an individual with diabetes. The term "treating" also includes an induction of a euglycemic response in the individual suffering from dis-regulated hyperglycemia. Euglycemia refers to the range of blood glucose levels clinically established as normal, or as above the range of hypoglycemia but below the range of hyperglycemia. Therefore, a euglycemic response refers to the stimulation of glucose uptake to reduce the plasma glucose concentration to normal levels. For most adults, this level corresponds to the range in concentration of about 60-105 mg/dL of blood glucose and generally between about 70-100 mg/dL, but can vary between individuals depending on, for example, the sex, age, weight, diet and overall health of the individual. Effective treatment of a diabetic individual, for example, would be a reduction in that individual's hyperglycemia, or elevated blood glucose levels, to normalized or euglycemic levels, with this reduction directly resulting from secretion of insulin. Alternatively, effective treatment would be a reduction in fasting blood glucose to levels less than or equal to about 126 mg/dL.

As used herein, the term "preventing" is intended to mean a forestalling of a clinical symptom indicative of diabetes. Such forestalling includes, for example, the maintenance of normal levels of blood glucose in an individual at risk of developing diabetes prior to the development of overt symptoms of the disease or prior to diagnosis of the disease. Therefore, the term "preventing" includes the prophylactic treatment of individuals to guard them from the occurrence of diabetes. Preventing diabetes in an individual is also intended to include inhibiting or arresting the development of the disease. Inhibiting or arresting the development of the disease includes, for example, inhibiting or arresting the occurrence of abnormal glucose metabolism such as the failure to transfer glucose from the plasma into the cells or failure to produce adequate insulin. Therefore, effective prevention of diabetes would include maintenance of glucose homeostasis due to glucose-regulated insulin expression in an individual predisposed to a diabetic condition, for example, an obese individual or an individual with a family history of diabetes. Inhibiting or arresting the development of the disease also includes, for example, inhibiting or arresting the progression of one or more pathological conditions or chronic complications associated with diabetes. T2DM is frequently associated with the related metabolic syndrome, characterized with obesity, high lipid, high blood pressure and cardiovascular diseases. Effective prevention and treatment for T2DM will lead to better diagnosis and management of the related metabolic syndrome.

The term "preclinical diabetes" refers to a stage before the onset of diabetes, where a patient has not shown any symptoms of diabetes, such as excessive sugar level, (see Table A for guidance), but will progress into diabetes in the future if no preventive remedy is provided. The preclinical diabetes is characterized by gradual beta cell loss that precedes clinical T1DM. The duration of the preclinical phase varies substantially, for example lasting for at least a few days, a few month, 1 year, 2 years, 5 years, or 10 years. The onset of the preclinical diabetes can be identified by examining whether there is any significant loss of beta cells, for example, by at least about 0.5%, about 1%, about 2%, about 5%, about 10%, about 30%, about 50%, about 60% or about 70% in a patient.

The term "beta cells", β-cells, and "beta cell mass" are used interchangeably herein and refer to a group of specialized cells that secrete insulin and are found in pancreatic islets. The morphological and functional characteristic of beta cells are well known in the art and discussed. Insulin increases the rate of synthesis of glycogen, fatty acids, and proteins and stimulates glycolysis and cell proliferation. It also promotes the transport of glucose, and some other sugars, and amino acids into muscle and fat cells. Insulin levels are regulated to maintain glycemic homeostasis, and an important mechanism for regulating insulin production, and hence insulin levels, is beta-cell mass. Beta cell mass change can be monitored by a variety of methods available in the art as reviewed by Souza et al., and generally by measuring the changes of Dopamine receptor levels in the pancreas of a patient. In one embodiment, such changes of Dopamine receptor levels indicates any significant loss or increase of beta cells in pancreas, for example, at least, about 0.5%, about 1%, about 2%, about 5%, about 10%, about 30%, about 50%, about 60% or about 70% loss of beta cells in a patient, or at least about 0.5%, about 1%, about 2%, about 5%, about 10%, about 30%, about 50%, about 60% or about 70% increase of beta cells in a patient The term "Dopamine receptor" refers to all kinds of receptors to Dopamine, including, but not limited to, D1-like receptors, by which dopamine activates adenylyl cyclase, and D2-like receptors, by which dopamine inhibits adenylyl cyclase. The D1-like receptors include the D1 and D5 receptors while D2-like receptors include the two isoforms of the D2 receptors, differing in the length of their precited third cytoplasmic loop, dubbed D2 short (D2s) and D2 long (D2L), D3, and D4 receptors. Generally, the dopamine receptors can specifically bind to Beta cells and act as a cellular localizer for beta cells. In one embodiment, the dopamine receptors are D2-like receptors.

The term "non-invasive method" used herein refers to a diagnostic procedure that does not require obtaining tissue or blood samples from a patient suspect of developing or about to develop diabetes or other Beta cell-related disease. Generally, beta cells are not required to be extracted from the patient body for a biopsy in the "non-invasive" procedure. The "non-invasive" procedure does not exclude a procedure that requires injection of an agent, for example, an imaging agent, into the patient.

The terms "imaging agent" when used herein refers to a detectable molecule that is capable of illustrating the image of one or a group of cells when detected under appropriate imaging methods, for example, microscopy, position emission tomography, single photon emission computed tomography, such as such as MRI diagnosis, X-ray diagnosis, radiation etc.

The term "labeled compound" when used herein refers to a detectable compound or composition which is conjugated directly or indirectly to the dopamine receptors so as to generate a "labeled" receptor. The label may be detectable by itself (e.g. radioisotope labels or fluorescent labels) or, in the case of an enzymatic label, may catalyze chemical alteration of a substrate compound or composition which is detectable.

The term "radio-labeled imaging agent", when used herein, refers to a detectable radioactive compound or composition, for example radioisotope which is conjugated directly or indirectly to the dopamine receptors so as to generate a "labeled" receptor. Exemplary radio-labeled imaging agents include, but not limited to, those that can be visualized under position emission tomography (PET) $^{18}$F-fallypride, $^{18}$F-desmethoxyfallypride, $^{11}$C-fallypride, $^{11}$C-desmethoxyfallypride, $^{11}$C-raclopride, or $^{11}$C-FLB457, as well as those that can be used in single photon emission computed tomography (SPECT) such as $^{123}$I-IBZM ($^{123}$I-iodobenzamide), $^{123}$I-epidepride and others known to those of skill in the art.

The term "therapeutic efficacy" when used herein, refers to therapeutic effect of a drug or candidate drug in treating diabetes, for example, reduce the symptom of diabetes and pre-diabetes of a patient. In an exemplary embodiment of the present invention, the therapeutic efficacy can be measured by monitoring the patient's blood sugar levels using the method routinely used in medical practice. The therapeutic efficacy can also be monitored by measuring beta cell mass density using the methods described herein.

The term "mammal" for the purposes of treatment and diagnosis refers to any animal classified as a mammal, including but not limited to, humans, sport, zoo, pet, and domestic or farm animals, such as dogs, cats, cattle, sheep, pigs, horses, and primates, such as monkeys. In one embodiment, the mammal is a human.

The terms "subject" or "patient," as used herein, are used interchangeably, and can refer to any animal, and generally refers to a mammal, that is the subject of an examination, treatment, analysis, test or diagnosis. In one embodiment, humans are the subject. A subject or patient may or may not have a disease or other pathological condition.

An "insulin-resistant disorder" is a disease, condition, or disorder resulting from a failure of the normal metabolic response of peripheral tissues (insensitivity) to the action of exogenous insulin, i.e., it is a condition where the presence of insulin produces a subnormal biological response. In clinical terms, insulin resistance is present when normal or elevated blood glucose levels persist in the face of normal or elevated levels of insulin. It represents, in essence, a glucose disposal inhibition, by which either basal or insulin-stimulated glycogen metabolism, or both, are reduced below normal levels. Insulin resistance plays a major role in Type 2 diabetes, as demonstrated by the fact that the hyperglycemia present in Type 2 diabetes can sometimes be reversed by diet or weight loss sufficient, apparently, to restore the sensitivity of peripheral tissues to insulin. The term includes abnormal glucose tolerance, as well as the many disorders in which insulin resistance plays a key role, such as obesity, diabetes mellitus, ovarian hyperandrogenism, and hypertension. In T2DM, reduction of insulin-producing cells may occur and predispose these patients to overt hyperglycemia.

Diabetes mellitus is the name given to a heterogeneous group of disorders that have in common abnormal glucose tolerance.

Insulin-dependent diabetes mellitus (IDDM) or type I diabetes, formerly called juvenile-onset diabetes, is characterized by absolute dependency on exogenous insulin. About 10% of all people with diabetes have this type.

Non-insulin-dependent diabetes mellitus (NIDDM) or type II diabetes, formerly referred to as adult-onset, maturity-onset, is characterized by gradual onset and hyperglycemia but no tendency to ketoacidosis except under extraordinary stress. People with NIDDM may take insulin to control hyperglycemia, but it is not absolutely required. About 60 to 70% of people with NIDDM are obese, and this type is sometimes subdivided into obese and nonobese categories. Eighty-five to 90% of all people with diabetes have this type.

Maturity-onset diabetes in the young (MODY) differs from NIDDM in that is has a clearly defined autosomal dominant inheritance pattern. The hyperglycemia in this type is generally quite mild. MODY is also characterized by a decreased frequency of the long-term complications of diabetes.

Diabetes may be secondary, as a result of direct ablation of the beta cells in association with pancreatitis, pancreatectomy, or hemochromatosis.

A separate category has been designated as gestational diabetes and refers to women whose diabetes first becomes manifest during pregnancy. Although the diabetes normally resolves upon delivery, over the following years over 50% of such women subsequently relapse into overt NIDDM.

Three types of acute complications generally occur: severe hyperglycemia associated with a hyperosmolar, non-ketotic state; severe hyperglycemia associated with ketoacidosis; and hypoglycemia. The chronic complications are generally classified into vascular and nonvascular. Macrovascular complications are caused by large vessel disease and the complications relate to the vascular system involved (e.g., cerebrovascular, coronary artery, and peripheral vascular disease). Microvascular complications are caused by small vessel disease and include retinopathy, renal glomerular disease (Kimmelstiel-Wilson disease), some of the neuropathies (mononeuropathies), and possibly cardiac and other small vessels. Non-vascular complications include cataracts and polyneuropathy, both peripheral and autonomic.

There are three basic types of diabetes mellitus, type I or insulin-dependent diabetes mellitus (IDDM), type II or non-insulin-dependent diabetes mellitus (NIDDM), and type A insulin resistance, although type A is relatively rare. Patients with either type I or type II diabetes can become insensitive to the effects of exogenous insulin through a variety of mechanisms. Type A insulin resistance results from either mutations in the insulin receptor gene or defects in post-receptor sites of action critical for glucose metabolism. Diabetic subjects can be easily recognized by the physician, and are characterized by hyperglycemia, impaired glucose tolerance, glycosylated hemoglobin and, in some instances, ketoacidosis associated with trauma or illness.

"Non-insulin dependent diabetes mellitus" or "NIDDM" refers to Type II diabetes. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988).

Symptoms and complications of diabetes to be treated as a disorder as defined herein include hyperglycemia, unsatisfactory glycemic control, ketoacidosis, insulin resistance, elevated growth hormone levels, elevated levels of glycosylated hemoglobin and advanced glycosylation end-products (AGE), dawn phenomenon, unsatisfactory lipid profile, vascular disease (e.g., atherosclerosis), microvascular disease, retinal disorders (e.g., proliferative diabetic retinopathy), renal disorders, neuropathy, complications of pregnancy (e.g., premature termination and birth defects) and the like. Included in the definition of treatment are such end points as, for example, increase in insulin sensitivity, reduction in insulin dosing while maintaining glycemic control, decrease in HbA1c, improved glycemic control, reduced vascular, renal, neural, retinal, and other diabetic complications, prevention or reduction of the "dawn phenomenon", improved lipid profile, reduced complications of pregnancy, and reduced ketoacidosis.

A "composition," as used herein, is defined as comprising dopamine receptor and a pharmaceutically acceptable carrier, such as water, minerals, proteins, and other excipients known to one skilled in the art.

The terms "disease," "disorder" and "condition" are used interchangeably herein, and refer to any disruption of normal body function, or the appearance of any type of pathology. The etiological agent causing the disruption of normal physiology may or may not be known. Furthermore, although two patients may be diagnosed with the same disorder, the particular symptoms displayed by those individuals may or may not be identical.

Administration "in combination with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

II. DETAILED DESCRIPTION

Dopamine Receptor as a Cellular Marker for Beta Cell Mass

Beta cells a group of specialized cells that secrete insulin and are found in pancreatic islets. Insulin increases the rate of synthesis of glycogen, fatty acids, and proteins and stimulates glycolysis and cell proliferation. It also promotes the transport of glucose, and some other sugars, and amino acids into muscle and fat cells. Insulin levels are regulated to maintain glycemic homeostasis, and an important mechanism for regulating insulin production, and hence insulin levels, is beta-cell mass.

During pregnancy (Marynissen et al., Diabetes 36:883-891, 1987) beta-cell mass increases, as well as in response to obesity (Kloppel et al., Surv. Synth. Pathol. Res. 4:110-125, 1985). These increases in beta-cell mass are attributed to an increased requirement for insulin to maintain normal glucose levels (Parsons et al., Endocrinology 130:1459-1466, 1992). It has also been shown that beta-cell mass normally decreases post-partum, primarily by apoptosis (Scaglia et al., Endocrinology 136:5461-5468, 1995).

It is generally believed that increases in beta-cell mass occurs in three ways: 1) an increase in cell size and function; 2) increased proliferation of mature beta-cells; and/or 3) increased, recruitment and differentiation of beta-cell progenitors. In diabetic mice, animals that received islet transplants and then achieved normal glycemia, showed beta-cell hypertrophy, rather than an increase in cell replication (Montana et al., J. Clin. Invest. 91:780-787, 1993). Adult beta-cell regeneration has been demonstrated in rodents (Hellerstrom et al., in "The Pathology of the Endocrine Pancreas in Diabetes", P. J. Lefebvre and D. G. Pipeleers, eds., pp. 141-170, Springer-Verlag, Heidelberg, 1988). In partially pancreatectomized rats both preexisting beta-cells, as well as proliferation and differentiation of precursor cells, have been demonstrated to expand (Bonner-Weir, Diabetes Nutr. Res. 5, Supp. 1:21-25, 1992).

Several factors have been shown to increase beta-cell mass. These factors include glucose (Woerner, Anal. Rev. 71:33-57, 1938), IGF-I (Rabinovitch et al., Diabetes 31:160-164, 1982), reg protein (Terazono et al., J. Biol. Chem. 263:2111, 1988), possibly a combination of TGF-alpha and gastrin (Bonner-Weir, Recent Prog. Hormone Res. 12:91-104, 1994), PPAR gamma agonist and GLP-1 agonist.

As discussed herein, beta cell mass can be monitored by a number of methods available in the art. However, none of the previous work has determined that D2R expression in the pancreas was confined to the endocrine pancreatic islets, or whether it was also present in the exocrine tissues. The present invention identified that D2R expression in the pancreas was confined to the endocrine pancreatic islets, and is not present in the exocrine tissues. Therefore, dopamine receptors can be used as a marker for bets cells. Using imaging techniques available in the art, labeled dopamine receptor can provide living cell imaging of beta cells.

The present invention is directed to a method of provide living cell imaging of beta cells comprising visualizing dopamine receptor in pancreas. Dopamine receptors, such as for example dopamine D2-like receptors, can be visualized with the standard techniques known in the art. In an exemplary embodiment of the present invention, immunological methods, such as immunohistochemical staining of cells or tissue sections of a human or an animal quantitate directly the expression of gene product of dopamine receptors. Dopamine receptors are labeled with a radioisotope or fluorescent labels. Standard immunostaining methods are also used to label the receptors which are then visualized with microscopy. The histochemical analysis even can be extended to the ultrastructure level under special conditions; fixation of pancreatic tissue intensifies the electron density of the vesicles containing the beta cells.

In yet another exemplary embodiment, mRNA encoding the dopamine receptors can be used to visualize dopamine receptors in pancreas with in situ hybridization method. The strand of noncoding DBA is applied to pancreas tissue sections under conditions suitable for hybridizing with endogenous (sense) mRNA. As the probes are radiolabeled, autoradiography reveals the beta cells containing the dopamine receptors.

In one embodiment of the present invention, the dopamine receptor/beta cells are visualized with a non-invasive method. When the non-invasive method is used, no tissue samples need to be obtained from the tested subject. An imaging agent comprising dopamine receptor is usually administered into a tested subject. The beta cells can then be visualized in the tested living subject under a number of detection approaches known in the art, including but not limited to, positron emission tomography (PET), single photo emission computed tomography (SPECT), MRI, CT, and the combinations thereof.

Visualization of beta cells provide key information on changes of beta cells, which are often a vital indicator of progression and development of beta-cells related disorders. The present invention is further directed to a method of monitoring changes in beta cell mass comprising detecting changes in levels of dopamine receptors in pancreas.

Changes in beta cell mass refers to any changes detectable by imaging signals of dopamine receptors, including but not limited to increase or decrease in number of beta cells (or density of beta cell mass) in pancreatic islet, or in functional or morphological state of the beta cells, for example, the robustness of cells, the morphological integrity of beta cells, etc. Beta cell mass density can be determined by counting the number of beta cell per $mm^2$ in a immunohistostained tissue slice under microscope. Alternatively, beta cell mass density can be determined by calculating the standard uptake value (SUV) of the imaging agents when the non-invasive methods, such as PET or SEPCT, are used.

In one aspect, changes in beta cells can be measured between any two different time points of the same subject to monitor the progression of beta-cell mass related disorders, such as diabetes. Decrease of the number of beta cells (or density of beta cell mass) in pancreas at a second time point compared to a first time point indicates that the disorder is aggravated. However, if a restoration of beta cells is discovered at a second time point compared to the first time point, the subject is making a good progress toward the treatment of the disorder. In another aspect, the beta cell mass of a subject may also be compared to a standard normal range so that if any significant loss in beta cells of a subject occurs, the subject may be likely to develop diabetes and will be closely monitored for any abnormal glucose intolerance. Therefore, monitoring the changes in beta cells in pancreatic islet allows a skilled artisan to predict and monitor the development or progression of beta-cell-related disorders, for example diabetes, even before any clinical symptoms of diabetes appear. In yet another aspect, beta cell changes are used as an indicator in evaluating a candidate drug for treating beta-cell related disorders. The degree of restoration of beta cells after being exposed to the candidate drug indicates the therapeutic potential the candidate drug has. This evaluation can be conducted in animal models first to determine the suitable dosage range of the candidate drugs.

Diagnosis of Diabetes and Management of Preventive and Treatment

Diabetes mellitus is a chronic disease characterized by relative or absolute deficiency of insulin which results in glucose intolerance. The term is intended to include all types of diabetes mellitus, including, for example, type I, type II, and genetic diabetes. Type I diabetes is also referred to as insulin dependent diabetes mellitus (IDDM) and also includes, for example, juvenile-onset diabetes mellitus. Type I is primarily due to the destruction of pancreatic beta-cells. Type II diabetes mellitus is also known as non-insulin dependent diabetes mellitus (NIDDM) and is characterized, in part, by impaired insulin release following a meal. Insulin resistance can also be a factor leading to the occurrence of type II diabetes mellitus. Genetic diabetes is due to mutations which interfere with the function and regulation of beta-cells.

Diabetes is characterized as a fasting level of blood glucose greater than or equal to about 140 mg/dl or as a plasma glucose level greater than or equal to about 200 mg/dl as assessed at about 2 hours following the oral administration of a glucose load of about 75 g. The term "diabetes" is also intended to include those individuals with hyperglycemia, including chronic hyperglycemia and impaired glucose tolerance. Plasma glucose levels in hyperglycemic individuals include, for example, glucose concentrations greater than normal as determined by reliable diagnostic indicators. Such hyperglycemic individuals are at risk or predisposed to developing overt clinical symptoms of diabetes mellitus. Examples of such pathological conditions associated with diabetes are listed in Table A.

TABLE A

Categories of Glucose Tolerance Impairment in Nonpregnant Adults

| Category | Fasting (mg/dl) | ½ h, 1 h, 1½ h OGTT value (mg/dl) | 2 h OGTT value (mg/dl) |
|---|---|---|---|
| Normal | <100[a] | <200 | <140 |
| Impaired glucose tolerance | 100-125 | ≥200 | 140-200 |
| Diabetes mellitus | >126[b] | ≥200 | ≥200 |

Source: Adapted from the National Diabetes Data Group categorization (National Diabetes Data Group, 1979; Diabetes Care, Vol 30, S42-S47, 2007).
[a]All values assume venous plasma glucose measured.
[b]Diagnosis of diabetes mellitus can be made if FBG > 126 on 2 separate days. If FBG < 126, then both 2 h sample and some other value between the fasting and 2 h value must both be ≥200 mg/dl.

The methods of the present invention is particularly useful in determining whether a subject is developing diabetes. In one embodiment of the present invention, the present invention is directed to non-invasive methods of predicting whether a subject is at preclinical stage of diabetes. The patient under test is typically at risk or predisposed to developing overt clinical symptoms of diabetes mellitus, such as abnormally high blood sugar level. This preclinical period are usually characterized by gradual Beta Cell Mass loss and precedes clinical T1DM. The duration of the preclinical phase varies substantially. The method of the present invention can determine whether a patient is at the preclinical state of a diabetes at least 1 day, 10 days, 30 days, 6 months, 1 year, 5 years, or 10 years before onset of overt clinical symptoms of diabetes mellitus. The methods of the present invention is sensitive and can detect at least about 10%, about 30%, about 50% or about 70% loss of beta cell mass. Loss of beta cell mass is determined by comparing the beta cell density illustrated by the intensity of labeled dopamine receptor of a tested subject to a range of normal values of the beta cell mass density for a human patient, which can be determined based on multiple times of observation of beta cell mass density illustrated by radio-labeled dopamine receptor.

Once a patient is diagnosed as being pre-diabetic, preventive remedies, such as proper management in diet or life style would be recommended by the doctor to prevent the deterioration of the situation. The above-described non-invasive diagnostic methods are very useful to continuously monitor the beta cell mass of said patient adopting such preventive remedies at a frequency of at least, for example, every week, every two weeks, every six week, every year, every two years, or every five years. The preventive remedies received by the patient can be adjusted according to the detected beta cell mass density every time after the detection. For instance, if the loss of beta cell mass stopped, or beta cell mass is restored, the adopted preventive remedy is proven to be effective. Otherwise, a more effective preventive remedy will be developed.

The methods of the present invention can also be used to diagnose diabetes after a patient has already developed clinical symptom for diabetes. Compared to the currently existing diagnosis method for diabetes, such as examine patient blood sugar level, the present methods offer advantage that no patient blood or tissue need to be extracted from the tested patient. Same as in the preclinical stage, a composition comprising a radio-labeled dopamine receptor imaging agent is administered into the tested patient. The beta cell mass density is then measured using the diagnostic imaging described herein. Abnormally low beta cell mass is determined by comparing the beta cell density illustrated by the intensity of labeled dopamine receptor of a tested subject to a range of normal values of the beta cell mass density for a healthy human subject, which can be determined based on multiple times of observation of beta cell mass density illustrated by radio-labeled dopamine receptor. A patient is usually considered as having diabetes if about 50%, about 60%, about 70%, about 80%, or about 90% loss of beta cell mass is detected. These diagnostic methods can be used in combination with other standard methods used in the art for clinical diagnosis of diabetes, such as measurement of patient blood sugar levels (see Table A), so that a better diagnostic profile of a patient is generated for designing a suitable therapeutic regimen.

The present invention offers non-invasive methods of monitoring progression of diabetes of a patient by detecting changes in levels of dopamine receptors in the pancreas of said patient. Same as in the preclinical stage, the level of a radio-labeled dopamine receptor, which indicates the density of beta cell mass in the pancreas of the patient are measured at any two or more time points (a first time point, a second time point, a third time point, etc). If the beta cell mass decreases or the morphological integrity of beta cells deteriorate at a second time point as compared to that at the first time point, the patient is becoming more diabetic. If the beta cell mass increases, or the morphological integrity of beta cells improves at a second time point as compared to that at the first time point, the patient is the patient is making a progression toward recovery.

The methods of monitoring the progression of the present invention are particularly useful in managing the treatment of diabetes in a patient. Current therapeutics for Type 1 diabetics are insulin or insulin mimetics, while most type 2 diabetic patients are treated either with agents that stimulate beta-cell function or enhance the patient's tissue sensitivity towards insulin. Several classes of drugs are available for diabetes therapy. These include: insulin, or insulin mimetics; insulin sensitizers including (a) biguanides such as Metformin (b) retinoid-X-receptor (RXR) and peroxisome proliferator activated receptor (PPAR) agonists, such as the Thiazolidinedione (glitazone) and PPAR-gamma agonists, e.g., Rosiglitazone and Troglitazone; (c) sulfonylureas (SU), such as Gliclazide, Glimepiride, Glipizide, Glyburide, Tolbutamide and Tolcyclamide; (d) amino acid and benzoic acid derivatives, such as Nateglinide and Repaglinide; (e) alpha-glucosidase inhibitors, such as Acarbose and miglitol; (f) cholesterol lowering agents, such as (i) HMG-CoA reductase inhibitors, e.g., Lovastatin, and other statins), (ii) bile acid sequestrants, e.g., Cholestyramine (iii) nicotinic acid, (iv) proliferator-activator receptor alpha-agonists, such as Benzafibrate, and Gemfibrozil, (v) cholesterol absorption inhibitors, e.g., beta-sitosterol and (vi) acyl CoenzymeA: cholesterol acyltransferase inhibitors, e.g., Melinamide; and (vi) Probucol.

The various modes of therapy used by the diabetic patients are also important.

Assessment of adherence to diet or compliance with an insulin regimen may reveal why control has worsened or hypoglycemic reactions occur. There is a rather large inter-individual variation in insulin time of action in this regard. The pattern of insulin site rotation may be important, as exercise shortly after injection of insulin into an exercising limb has been shown to affect insulin absorption dramatically.

Various factors discussed above should be considered when design a treatment regimen for a diabetes patient, including, but not limited to, type of drugs used; the dosage of the used drug, modes of administration of the drug, time and frequency of administering the drug; and patient diet. In one aspect of the invention, one drug is sufficient to control the further development of diabetes. In another aspect of the invention, combination of two or more drugs are needed for achieve the desired treatment efficacy. After a treatment regimen is designed and implemented, the number and morphology of pancreatic beta cells in the patient are closely monitored with the methods described herein, at a frequency of at least, for example, every week, every two weeks, every six week, or every year. The regimen will be evaluated and adjusted depending on the changes of beta cell mass density or beta cell morphology in response to the treatment. After a multiple times of adjustments, an individualized optimal therapeutic regimen can be developed for the patient.

The above described methods are non-invasive methods, wherein no blood and tissues need to be extracted from a patient when they are used. The tested patient only needs to be injected with a composition comprising a radio-labeled dopamine receptor In detecting the Beta cell loss of a subject for the purpose of monitoring the progression or diagnosis of diabetes of the subject discussed above, a composition comprising a dopamine receptor imaging agent, for example radio-labeled dopamine receptor, is typically, administered into a tested subject. The composition can be administered into the subject parentally, for example, intravenously, intra-muscularly or subcutaneously. The composition used for diagnosis typically have the imaging agent dissolved in saline solution and has a pH value of about 5.0 to about 8.0, or alternately, a pH value of about 6.0 to about 7.0. Before being administered into a human subject, pyrogenicity and sterility are examined and ensured for human use compliance. A number of approaches are available in the art to detect the imaging signal of the imaging agent administered into the subject.

The present invention is directed to a method of managing treatment of diabetes in a patient comprising monitoring beta cell density of pancreas of said patient.

Non-Invasive Diagnostic Imaging Techniques

A variety of non-invasive diagnostic imaging techniques are available, including, but not limited to, positron emission tomography (PET), single photo emission computed tomography (SPECT), Magnetic Resonance Imaging (MRI) and computer assisted tomography (CT).

Nuclear imaging of beta cells in pancreatic islet requires isotopes of elements with low atomic numbers e.g., hydrogen, carbon, nitrogen, and oxygen) that are constituents of biologically important compounds. However, these elements have few isotopes that emit gamma rays and their very short half-lives (seconds) make their clinical use impractical. Moreover, when gamma-emitting atoms are substituted, the activity of these compounds is usually altered. More useful are isotopes of elements that decay after longer half-lives (minutes to hours), and emit positrons (positively charged electrons). Radioactive isotopes of carbon ($^{11}C$), nitrogen ($^{13}N$), or oxygen ($^{15}O$) can be substituted in the structure of any of the compounds to be investigated; fluorine ($^{18}F$) can be substituted for hydrogen. Biological activity is preserved when a radioactive atom that decays by positron emission substitutes for a similar atom of low atomic number.

By binding positron-emitting isotopes to components of biological interest, a variety of biochemical processes or structures can be examined. For example, beta cell can be probed by using a radioactive dopamine receptor analog and the density of the beta cell mass is monitored in pancreas by administering radiolabeled dopamine receptors. Position emission tomography is an extraordinarily sensitive analytical tool; it can detect picomolar changes in appropriately labeled chemical compounds.

Useful positron-emitting isotopes can be made in a cyclotron by accelerating protons into the nuclei of nitrogen, oxygen, carbon, and fluorine. Normally, these nuclei contain protons and neutrons in equal numbers. Incorporation of an extra proton into the nucleus produces an unstable isotope. For stability to be regained, the proton is broken down into two particles: (1) a neutron, which remains within the nucleus because a stable nucleus can contain extra neutrons; and (2) a positron, an unstable particle, which travels away from the site of generation, dissipating energy as it goes. The positron eventually collides with an electron, and the collision leads to their mutual annihilation and the emission of two gamma rays at precisely 180° from one another.

The two gamma rays emitted by the annihilation of a positron and electron ultimately reach a pair of detectors that will record an event when, and only when, two simultaneous detections are made. This method of coincident detection permits precise localization of the site of gamma emission. The resolution of PET is between 2.5 and 6 mm.

Selection of a suitable isotope for PET imaging is an important step. In general, it is highly desirable the isotope does not have decays other than 511-keV positron emission. This will minimize the impairment of the spatial resolution due to energy and will reduce the radiation burden to the patient. A generator-based isotope is needed due to the high specific activity for receptor-based target specific radiopharmaceuticals. It is also much easier for transportation, delivery, and quality control using a generator produced isotope. The half-life of the parent isotope should be long while the half-life of the corresponding daughter isotope should be short. In addition, the cost for the production of the parent isotope and availability of the enriched source (for the production of the parent isotope) should also be considered. $^{18}F$ is a cyclotron-produced PET isotope. The relatively long half-life ($t_{1/2}$=110 min) makes it possible for regional suppliers to ship $^{18}F$-FDG radiotracers to the clinical sites and for clinicians to collect useful images. $^{18}F$ can be readily incorporated into endogenous biological compounds such as 2-deoxy-D-glucose. Following the foot-step of MRI, recent developments of mobile trailers for FDG PET imaging has made it possible for small institutions to have access to state-of-art PET services.

If the PET isotope is $^{18}$F, the target-specific PET radiopharmaceutical can be readily prepared according to the known procedures (Vaidyanathan, G. and Zalutsky, M. R. Bioconjugate Chem. 1990, 1, 269-273; Vaidyanathan, G. and Zalutsky, M. R. Nucl. Med. Biol. 1992, 19, 275-281; Vaidyanathan, G. and Zalutsky, M. R. Bioconjugate Chem. 1994, 5, 352-364; Vaidyanathan, G. and Zalutsky, M. R. Nucl. Med. Biol. 1995, 22, 759-764; Sutcliffe-Goulden et al. Bioorg. Med. Chem. Lett. 2000, 10, 1501-1503).

In a one embodiment of the present invention, the PET radiopharmaceutical is $^{18}$F-fallypride (see structure shown in FIG. 1), $^{18}$F-desmethoxyfallypride, $^{11}$C-fallypride, $^{11}$C-desmethoxyfallypride, $^{11}$C-raclopride, or $^{11}$C-FLB457.

Like positron emission tomography, magnetic resonance imaging (MRI) is based on computerized tomography and can be used to explore function as well as structure, but with much better spatial resolution. Magnetic resonance technology was first developed in the early 1950s to measure the atomic constituents of chemical samples. Later it was combined with computerized tomography to provide images that localize atomic nuclei. This combination resulted in a powerful imaging technique that can distinguish different body tissues because of their individual chemical compositions. For example, gray matter can be strikingly differentiated from white matter, more so than by computerized tomography. As a result, the spatial resolution of MRI is comparable to that of fixed and sectioned anatomical material. Many of the key anatomical structures that were discussed in the previous three chapters can be clearly seen in MRI sections of the living brain.

When elements with an odd atomic weight, such as hydrogen, are exposed to a strong static homogeneous magnetic field, the nuclei behave as spinning magnets and develop a net alignment of their spin axes along the direction of the applied field. The atomic nuclei give rise to the magnetic resonance imaging (MRI) signal in the following way. The alignment of the spin axes can be perturbed by a brief pulse of radio waves, which saves to tip the spinning nuclei away from their parallel orientation with the strong magnetic field and provides energy for their subsequent gyroscope-like motions, called precession.

When the pulse is turned off, the nuclei tend to return to their original orientation, and in doing so release energy in the form of radio waves. The frequency of the radio wave given off is distinct for different atomic species as well as for a given atomic nucleus in different chemical or physical environments. The resonating nuclei thus become radio wave transmitters with characteristic frequencies and reveal their presence by their signals.

Different nuclear species absorb energy from radio waves of a particular frequency. The ability of the atomic nuclei to absorb energy from radio waves is called nuclear magnetic resonance. The atomic nuclei, having absorbed energy from the externally applied radio waves, then release it as a signal as they return to a lower-energy state.

The rate at which nuclei return to a lower-energy state is called relaxation and is usually described by its time constant (T). There are two types of relaxation of importance in MRI at present: spin-lattice relaxation ($T_1$) and spin-spin relaxation ($T_2$). For a particular atom, these relaxation times vary from compound to compound. For example, hydrogen has a much shorter relaxation time in fat than it has in water. Relaxation times also vary according to the local tissue conditions, such as water in the cerebrospinal fluid and water in the brain parenchyma. (Dense bone, which contains little water, is invisible on such images.) Since relaxation times are influenced by local tissue conditions, by emphasizing one or the other relaxation time an image can either discriminate between normal tissues of various composition or define pathological processes. For example, the difference between gray and white matter is best visualized by images emphasizing $T_1$ whereas cerebrospinal fluid is greatly enhanced on images emphasizing $T_1$.

Images can be generated that depict either the distribution of a particular relaxation time in a cross section of tissue or the actual concentration of a particular atomic nucleus. In MRI the greatest contrast is obtained when images represent tissue relaxation times rather than proton concentration. For example, the differences between the relaxation times of gray and white matter or white matter and cerebrospinal fluid are much greater than the differences between their proton concentrations.

Computerized Tomography

In computerized tomography (CT) a series of narrow, highly restricted beams of radiation are projected from the X-ray tube onto scintillation crystals, which are more sensitive than X-ray film. An X-ray source is rotated 180° around one side of the skull while the X-ray detectors are rotated around the opposite side. At each degree of rotation a series of transmission measurements is made (up to several hundred, depending on the model). The radiodensity of a single region of tissue is calculated by summing the readings of all beams passing through that region. The spatial resolution of CT scans is determined by the distance between these intersection points. The result for each section of brain is a matrix of attenuation coefficients computed from thousands of radiation intensity measurements and visually displayed as dark and light areas.

Computer-analyzed X-ray transmission profiles are able to resolve gray and white matter, blood, and cerebrospinal fluid, despite very small differences in radiodensity (less than 2%). Currently available CT equipment can produce scans with a resolution of less than 1 mm in soft tissue.

Intravenous injection of iodinated radiopaque material further enhances the contrast between tissue constituents in regions that have either increased vasculature or impaired blood-brain barrier functions. By this means, blood vessels, tumors, or abscesses can be effectively visualized. In recent years, there has been considerable progress in the development of techniques to co-register and align functional and anatomical images. This has been driven primarily by the demand for accurate localization of cerebral function visualized in PET studies where the low resolution morphology is, in most cases, insufficient to identify the related cerebral structures. Techniques to overcome this problem have been developed based, for example, on the identification of certain geometrical features common to both imaging modalities. For example, A. C. Evans et al, J Cereb Blood Flow Metab 11(2), A69-A78 (1991) teach the use of landmark matching while D. G. Thomas et al., "Use of relocatable stereotactic frame to integrate positron emission tomography and computed tomography images: application to human malignant brain tumors," Stereotactic and Functional Neurosurgery 54-55, 388-392 (1990) teach the use of externally-placed reference or fiducial markers. Identification of the skull and brain contour from either the PET transmission or emission scan and the MR or CT scan has also been employed as an alignment technique by C. A. Pelizzari et al, "Accurate three-dimensional registration of CT, PET and MR images of the brain," J Comp Assist Tomogr 13, 2026 (1989). Following the identification of common structures in the two modalities, a rigid-body transformation is used to rotate and translate the MR or CT scan into the reference frame of the PET image, accounting for differences in pixel size between the two imaging modalities. A technique which uses a least squares approach to minimize the distribution of pixel-to-pixel ratios between the two images requiring alignment has proved successful both for PET to PET by R. P. Woods et al., "Rapid automated algorithm for aligning and reslicing PET images," J Comp Assist Tomogr 16, 620-633 (1992); and PET to MR by R. P. Woods et al, "MRI-PET registration with an automated algorithm," J Comp Assist Tomogr 17, 536-546 (1993). An interactive method has also been published U. Pietrzyk et al, "Three-dimensional alignment of functional and morphological tomograms," J Comp Assist Tomogr 14(1), 51-59 (1990), wherein a human observer makes alignment decisions based on visual inspection of images of brain sections displayed on a computer screen.

After two images from different modalities are aligned they can be displayed in a number of ways, such as, for example, side by side with linked cross-hair cursors, so that positional correspondence between the two image sets is easily established. This type of software tool is now readily available commercially. A different technique that is more appropriate for this project is that of image fusion, in which the two different image sets are combined into a single image so that positional correspondence is automatically established. Fusion techniques in general consist of either statistical methods or color-wash methods. Color-wash methods assign a color scale to one image and an intensity scale to the other image, whereas statistical methods select the most significant values from each image and assign as many orthogonal colors to each as possible for the particular display device.

Essentially all the registration techniques mentioned above have been developed for use in cerebral studies, and in particular brain activation. This is to some extent because PET images of cerebral flow and metabolism already contain a limited amount of low-resolution anatomical information which can be effectively exploited by the alignment procedures. However, the problems of alignment and co-registration in other regions of the human body are more difficult to solve owing to the absence of even low-resolution morphology in the functional image. This is particularly acute in the abdomen, where the PET emission scan shows little or no anatomical detail. Furthermore, the advantage of co-registering organs other than the brain has been recognized only recently, with, as described above, a rapid growth in the use of FDG in oncology.

It is evident, therefore, that in regions such as the thorax and abdomen, the demonstration of increased FDG uptake is limited in value without an unambiguous localization of tracer uptake to a specific structure (e.g. a tumor) seen on the corresponding CT image. It is desirable, therefore, to accomplish accurate registration of anatomical data, such as is obtained with CT, to improve the use of PET imaging in all of the above applications in oncology. In the discrimination of a benign versus a malignant mass, a CT scan typically defines the borders of the mass and co-registration with PET allows a more accurate quantitative evaluation. In certain organs, where nearby structures have a high concentration of excreted tracers, such as FDG in the renal pelvis, exact registration of PET and CT allows a finer discrimination of the etiology of a "hot spot", thus reducing the likelihood of falsely identifying the mass as a tumor, or misjudging a focal accumulation of tracer as probable urine activity. For future tracers which may have labeled metabolites excreted via the hepatobiliary system and bowel this may be even more crucial.

EXAMPLES

2.1 General Methods

All chemicals and solvents were of analytical or HPLC grade from Aldrich Chemical Co. and Fisher Scientific. Electrospray mass spectra were obtained on a Model 7250 mass spectrometer (Micromass LCT). Proton NMR spectra were recorded on a Bruker OMEGA 500 MHz spectrometer. Analytical thin layer chromatography (TLC) was carried out on silica coated plates (Baker-Flex, Phillipsburg, N.J.). Chromatographic separations were carried out on preparative TLC (silica gel GF 20×20 cm 2000 micron thick; Alltech Assoc. Inc., Deerfield, Ill.) or silica gel flash column or semi-preparative reverse-phase columns using the Gilson high performance liquid chromatography (HPLC) systems. High specific activity $^{18}$F-fluoride was produced in the MC-17 cyclotron or the CTI RDS-112 cyclotron using oxygen-18 enriched water ($^{18}$O to $^{18}$F using p, n reaction). The high specific activity $^{18}$F-fluoride was used in subsequent reactions which were carried out in automated radiosynthesis units (either a chemistry processing control unit (CPCU or a nuclear interface fluorine-18 module). Fluorine-18 radioactivity was counted in a Capintec dose calibrator while low level counting was carried out in a well-counter (Cobra quantum, Packard Instruments Co., Boston, Mass.). Radioactive thin layer chromatographs were obtained by scanning in a Bioscan system 200 Imaging scanner (Bioscan, Inc., Washington, D.C.). Rat brain slices were obtained on a Leica 1850 cryotome. Fluorine-18 autoradiographic studies were carried out by exposing tissue samples on storage phosphor screens. The apposed phosphor screens were read and analyzed by OptiQuant acquisition and analysis program of the Cyclone Storage Phosphor System (Packard Instruments Co., Boston, Mass.). All animal studies were approved by the Institutional Animal Care and Use Committee of University of California-Irvine. Human studies were approved by the Institutional Review Board of Kettering Medical Center.

2.2 Radiopharmaceutical

The synthesis of $^{18}$F-fallypride was carried out in the chemical process control unit (CPCU) of the CTI RDS-112 cyclotron using previously reported methods (Mukherjee et al., Nucl Med Biol 1995 22:283). Purification of $^{18}$F-fallypride was carried out by reverse-phase high performance liquid chromatographic (HPLC) separation on a C-18 column (Alltech Inc., Deerfield, Ill.) using acetonitrile (58%) and triethylamine (0.1%) in water at a flow rate of 2.5 ml/min in a gradient Gilson HPLC system. The radioactive fraction appearing at 20 mins was collected and all solvents were removed from the product by rotary evaporation in vacuo. The product was taken in sterile saline, passed through a Whatman 0.22 μm polytetrafluoroethylene (PTFE) filter. This final product was tested for pyrogenicity and sterility for human use compliance. The pH of the sterile injectable radiopharmaceutical was in the range of 6-7. Radioactive thin layer chromatography was used to check radiochemical purity (eluting solvent: 95% acetonitrile in water, $R_f$=0.43 in silica stationary phase). Gas chromatography (SRL 8610C gas chromatograph, consisting of a flame ionization detector; Supel Cowax 10 column at 40° C. for 2 min to a final temperature of 130° C. with a ramp rate of 20° C./min) was used to ascertain removal of all organic solvents in the final radiopharmaceutical stock solution (retention times: ethanol 1.9 min, acetonitrile 2.6 min, triethylamine 4.8 min). Specific activity of the product was measured on the Gilson HPLC using the aforementioned conditions with a standard curve of unlabeled fallypride and was found to be 2800±300 Ci/mmol. The radioligand was typically purified in approximately 20-40 mCi batches. The final sterile 0.9% saline solution of $^{18}$F-fallypride (range of 5 to 6.7 mCi, depending on the weight of subject) was dispensed for intravenous injection.

2.3 Rodent Studies

Male Sprague-Dawley rats (200-250 g) or male Lewis rats (100-150 g) were anesthetized and decapitated. The brain and pancreas was rapidly removed and frozen in isopentane at −20° C. Horizontal slices of pancreas were cut to 10 μm thickness using a Leica 1850 cryotome. Slices were stored at −20° C. Slices were preincubated for 10 minutes in 50 mM Tris-HCl, 120 mM NaCl, 5 mM KCl buffer (pH 7.4). Slices were then incubated with 1-2 μCi/cc of $^{18}$F-fallypride at 37° C. for 1 hour. Nonspecific binding was measured by challenging $^{18}$F-fallypride with the antagonist haloperidol (100 μM) and the agonist dopamine (100 μM). After incubation, slices were rinsed twice for 2 min in ice-cold buffer, dipped briefly in ice-cold water, blown dry and laid out for autoradiography. Slides with tissue samples were exposed to a multipurpose storage phosphor screen for 24 hours and developed; the autoradiographs were generated using the Phosphor Cyclone Imager (Packard Instruments Co.) The amount of binding in the pancreas was measured as digital light units, DLU/mm$^2$. Autoradiographs were quantified using a computer-based image analysis system (OptiQuant Version 4.0 Packard Instruments Co., Boston Mass.).

For ex vivo studies, Lewis rats were anesthetized with halothane and injected intravenously with $^{18}$F-fallypride (0.1 to 0.2 mCi). The rats were then sacrificed at either 60 or 120 min post-injection. The brain and pancreas were isolated and sectioned to 10 μm and 40 μm sections. Slides with tissue samples were exposed to a multipurpose storage phosphor screen for 24 hours and developed; the autoradiographs were generated using the Phosphor Cyclone Imager (Packard Instruments Co.). Brain slices contained the striata, cerebellum and other regions known to contain D2R. The amount of binding to the striata, cerebellum and pancreas was measured as digital light units, DLU/mm$^2$. Autoradiographs were quantified using a computer-based image analysis system (OptiQuant Version 4.0 Packard Instruments Co., Boston Mass.).

Male Sprague-Dawley rats were used to develop a model for diabetes. Streptozotocin (STZ) (80 mg/kg body weight, i.p. injection) chemically destroyed beta-cells and induced diabetes in adult male Sprague-Dawley rats (Lai et al., Am J Physiol Endocrinol Metab 2007 292:E292). Blood glucose was monitored by tail vein-sampling. Diabetic rats were harvested 7 days after the onset of diabetes. $^{18}$F-fallypride binding to pancreatic and brain sections was done for three pairs of STZ- and age-matched rats. Regions of Interest (ROI) that designate a volume in space over which statistics can be calculated, were gathered from autoradiograms of brain and pancreatic tissues incubated with $^{18}$F-fallypride (total binding) as well as adjacent tissue slices incubated with $^{18}$F-fallypride in the presence of 10 μM haloperidol (nonspecific binding). Specific binding was determined for each animal by subtracting nonspecific binding, measured in digital light units per mm$^2$ (DLU/mm$^2$), from total binding for adjacent tissue sections in brain and pancreas.

2.4 Human Subjects

PET and PET/CT studies were done on healthy control subjects. Medical histories of the subjects and written informed consent were given prior to scanning. It was ascertained that the subjects were not on any medications that might affect $^{18}$F-fallypride binding. All subjects refrained from either alcohol or caffeine for at least four hours prior to each test session in order to preclude any possible influence on receptor binding of $^{18}$F-fallypride. Women of child bearing age underwent a pregnancy test and were excluded from the study if found pregnant. The study was approved by the radioactive drug research committee and the institutional review board of Kettering Medical Center.

2.5 PET Studies in Human Subjects

The subjects were prepared by placing one intravenous catheter in one arm for administration of the $^{18}$F-fallypride. The subjects were then positioned in the PET scanner, and their alignment was marked for purposes of repositioning. The subjects were requested to lay still during the PET data acquisition in the dimly lit quiet room but were free to open/shut their eyes. The PET data was acquired with an EXACT HR+ PET scanner (in-plane FWHM=4.6 mm, axial FWHM=3.5 mm, axial FOV=15.52 cm). A 5-minute transmission scan using $^{68}$Ge/$^{68}$Ga rod sources was acquired prior to administration of the radiopharmaceutical. Scanning was initiated with a 30-second bolus infusion of the radiopharmaceutical followed by a saline flush. A $^{18}$F-fallypride dose of approximately 0.07 mCi/kg was administered to each of the subjects (subjects weight ranged between 70 to 95 kg). The dynamic scanning sequence consisted of 6 frames at 30 seconds, 7 frames at 1 minute, 5 frames at 2 minutes, 4 frames at 5 minutes and 4 frames at 10 minutes. The subject was marked for repositioning and then removed from the scanner for a 20-minute break period. A second dynamic sequence with 8 frames at 10 minutes each was acquired, yielding a total study time of approximately 3 hours. The data set was reconstructed using the ECAT v 7.2 software, with an OSEM algorithm (3 iterations, 16 subsets). In order to evaluate reproducibility of PET measurements, following a period of 4-6 weeks, the subjects were scanned again in a similar fashion. A single T1-weighted MRI scan was acquired on a GE 1.5T scanner for all subjects for the purpose of anatomical definition of structures in the brain.

2.6 PET/CT Studies

The subjects were prepared by intravenous administration of $^{18}$F-fallypride. After 80 minutes, the subjects were then positioned in the Siemen's PET/CT Biograph. The subjects were requested to lay still during the PET/CT data acquisition in the dimly lit quiet room but were free to open/shut their eyes. Static scans of 10 mins duration each were acquired at different bed positions.

2.7 Image Analysis of Human Studies

The reconstructed dynamic PET data sets were first realigned to a reference summed image (50-80 minutes) to correct for patient motion and slight differences in positioning between the dynamic scans. These dynamic data sets were then used to create time-activity curves as well as pixel-by-pixel parametric images of the distribution volume ratio (DVR). The cerebellum (cerebellar lobes) was chosen as the reference region, having a minimal amount of specific binding to dopaminergic sites. The PET/CT data was analyzed to provide standard uptake values (SUV) in different organs which were identified using the CT image.

3. Results

Figure 2:
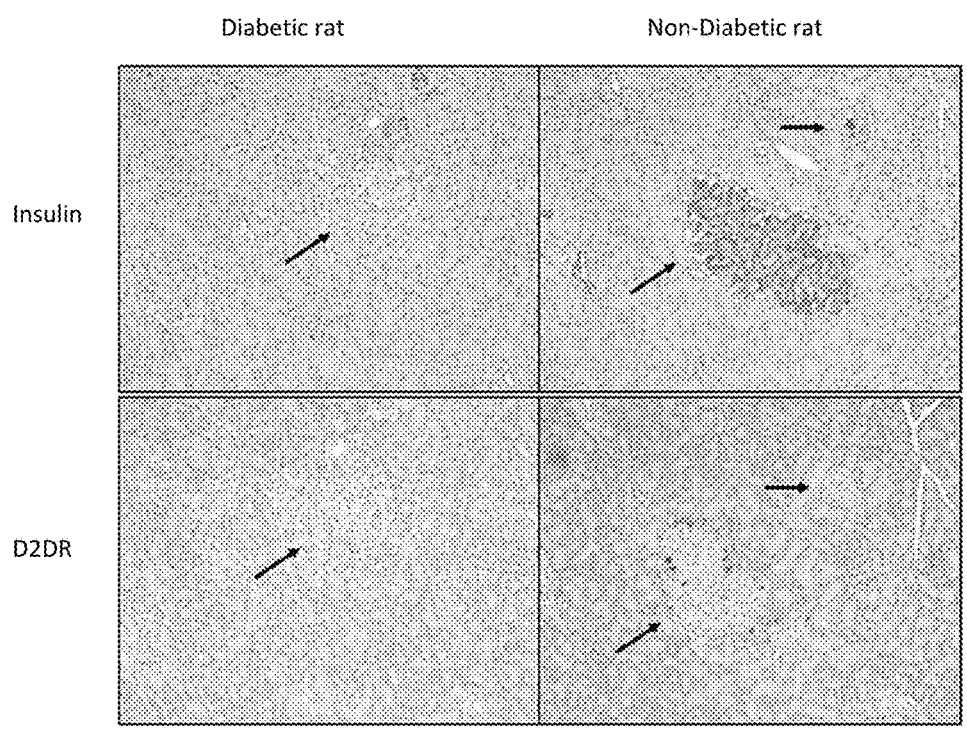
FIG. 2 is a picture of D2R expression in pancreatic islets, which shows that D2R is expressed in pancreatic islets but not in exocrine pancreas, suggesting that when diabetic prone BB/W rats develop diabetes, they lose insulin-expressing beta cells and concomitantly D2R expression is reduced (arrows showing specific areas of insulin receptors and D2R binding).

3.1 D2R are Expressed in Pancreatic Islets But not Pancreatic Exocrine Cells D2R expression has been demonstrated on rodent and human beta-cells using isolated islets and beta cell lines. D2Rs co-localized with insulin in intracellular granules. Quinpirole, a D2R agonist, inhibited glucose-dependent insulin secretion (Rubi et al., J Biol Chem 2005 280:36824). The paper by Rubi and colleagues did not determine whether D2R expression in the pancreas was confined to pancreatic islets, or whether it was also present in the exocrine tissues. FIG. 2 shows that D2R expression in pancreatic islets but not exocrine pancreas. FIG. 2 also shows that when diabetic prone BB/W rats develop diabetes, they lose insulin-expressing beta cells and concomitantly D2R expression is reduced.

Figure 3:
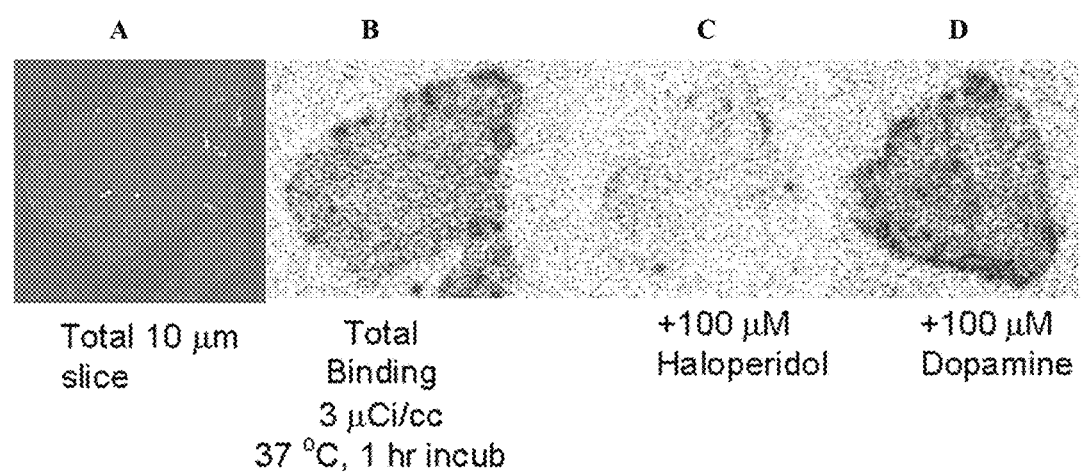
FIG. 3 is an autoradiography of rat pancreatic section showing $^{18}$F-Fallypride binding in sections of Lewis rat pancreas in vitro. A: 10 µm section of pancreas; B: $^{18}$F-Fallypride binding in the 10 µm section of pancreas section; C: $^{18}$F-Fallypride binding in the presence of 100 µM haloperidol; D: $^{18}$F-Fallypride binding in the presence of 100 µM dopamine.

3.2 $^{18}$F-Fallypride Binding in Rat Pancreas $^{18}$F-Fallypride binds to rat pancreatic sections (FIG. 3). Haloperidol, a lipophilic D2R antagonist, competitively displaces $^{18}$F-fallypride binding to the pancreas (FIG. 3). Dopamine, an agonist of D2R that cannot diffuse across the plasma membrane, does not displace $^{18}$F-fallypride binding. Together, these results suggest that $^{18}$F-fallypride binding to the pancreas is specific and to D2R.

Figure 4:
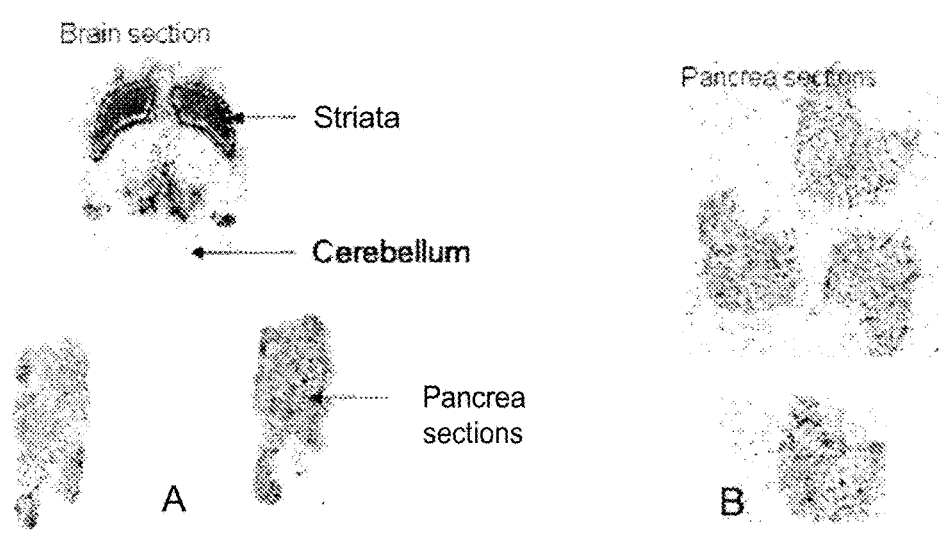
FIG. 4 is a an autoradiography of rat pancreatic and brain section showing $^{18}$F-Fallypride binding in sections of Lewis rat pancreas studied ex vivo. A: Rat sacrificed at 60 min post-injection showing brain section in the top and pancreas slices at the bottom; B: Rat sacrificed 120 min post-injection showing slices of pancreas.

3.3 $^{18}$F-Fallypride Binds to Rat Pancreas as Demonstrated in Ex Vivo Study Lewis rats were injected with $^{18}$F-fallypride; one rat was killed at 60 mins and the brain and pancreas of this rat were sectioned. A second rat was killed at 120 min and the pancreas were sectioned. FIG. 4 shows brain slices (30 microns) and pancreas slices (20 microns). Striatum (in red) showed highest binding in the brain and cerebellum very little. Pancreas showed binding which was found to be greater than cerebellum. Ratio of striatum to cerebellum was 55.3 and pancreas to cerebellum was 5.3. Rat #2 killed at 120 min also showed significant amount of binding in the pancreas, indicating binding and retention of $^{18}$F-fallypride.

Figure 5:
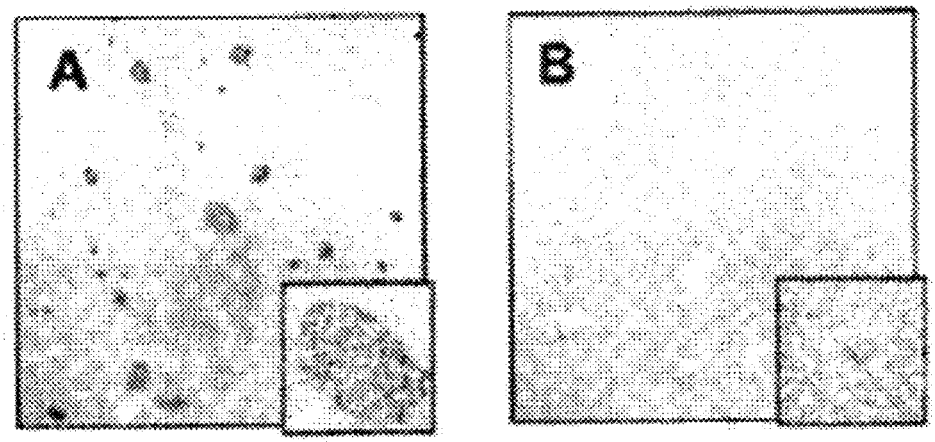
FIG. 5 is an autoradiography of rat section showing reduced $^{18}$F-fallypride binding to pancreas from STZ-treated rats compared to controls. Pancreas of control (A) and STZ-treated (B) rats stained for insulin (4×). Note absence of brown insulin-expressing cells in STZ rats. The insets show islets stained for insulin (40×).

3.4 $^{18}$F-Fallypride Binds to Rat Pancreas in Streptozotocin Treated Rats Immunostaining for insulin showed dramatic loss of BCM in streptozotocin-treated rats as seen in FIG. 5 (A: control rat and B: streptozotocin-treated rat). Adjacent pancreas sections from the control and streptozotocin group were treated with $^{18}$F-fallypride. Specific $^{18}$F-fallypride binding was reduced by ~70% in the pancreas of STZ-treated rats (p<0.05) corresponding to the loss of insulin staining, but there was no change in $^{18}$F-fallypride binding to control tissues—striatum and cerebellum (Table-1).

TABLE 1

$^{18}$F-Fallypride binding in control and streptozotocin treated male Sprague-Dawley rats

| Animal Group | Pancreas (DLU/mm$^2$) | Striatum (DLU/mm$^2$) | Cerebellum (DLU/mm$^2$) |
| --- | --- | --- | --- |
| Control | 1393 ± 479 | 121,167 ± 41,190 | 1597 ± 1382 |
| Streptozotocin | 310 ± 303 p < 0.05 | 112,059 ± 35,271 | 1119 ± 632 |

3.5 Human PET Imaging with $^{18}$F-Fallypride

Imaging in Brain

Figure 6:
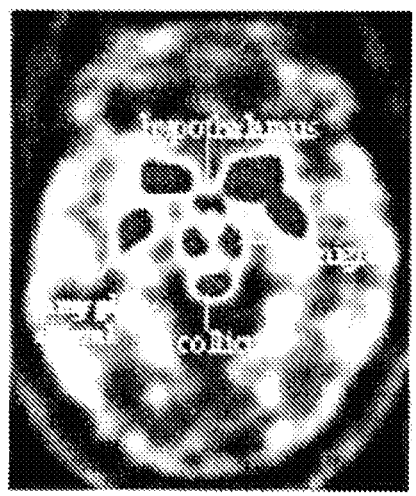
FIG. 6 is an image of human brain of $^{18}$F-fallypride PET in a normal volunteer showing binding to various regions including the hypothalamus.

Quantitative measures of $^{18}$F-fallypride binding in the human brain have been previously reported (Mukherjee et al. Synapse 2002 46:170). Distribution of $^{18}$F-fallypride was consistent in all subjects studied and the rank order of receptor concentration was putamen>caudate>thalamus=pituitary>amygdala> hypothalamus>colliculi>substantia nigra>hippocampus=temporal cortex>parietal cortex=occipital cortex=orbitofrontal cortex. For younger subject, BP ranged from 37 for the putamen to 0.4 for orbitofrontal cortex, with a test-retest error of about 10%. Both hydrophilic and lipophilic metabolites were observed in arterial blood plasma and analyses showed approx. 30-40% of plasma radioactivity at 3 hr was $^{18}$F-fallypride. With aging, all brain regions exhibited a significant decrease (>10% per decade) in binding of $^{18}$F-fallypride. PET studies with $^{18}$F-fallypride are thus suitable to study changes in D2/D3 receptors in striatal and extrastriatal brain regions. Regions such as hypothalamus which may have a role in diabetic patients was clearly visualized (FIG. 6).

3.5.2 Imaging in Pancreas

Figure 7:
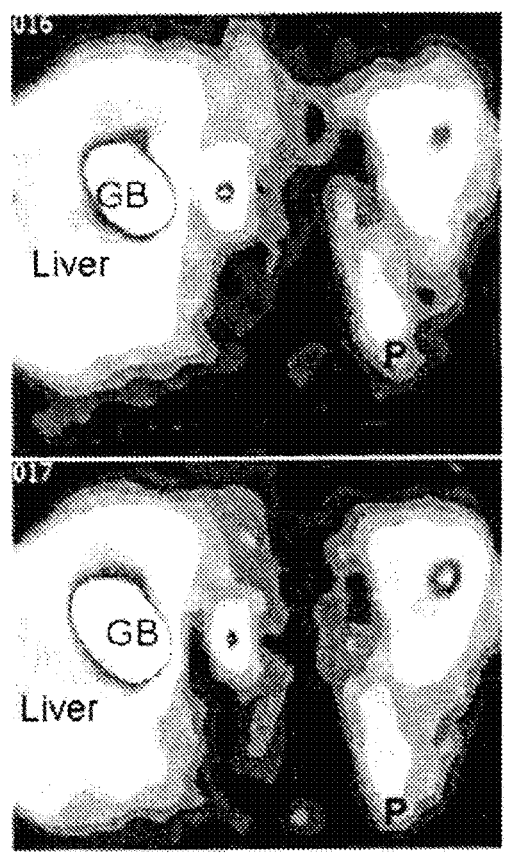
FIG. 7 is an image of human pancreas of $^{18}$F-fallypride PET showing localization in gall bladder (GB), liver and pancreas (P).

After 80 mins post injection of $^{18}$F-fallypride in a healthy volunteer, the region of the pancreas was imaged using a whole body HR+ PET scanner. FIG. 7 shows two PET slices with fallypride binding in comparison to a CT scan of a normal individual taken from the literature. The highest radioactivity (GB) is the gall bladder. The liver is also seen. The region that approximately corresponds to pancreas is marked "P" both in the CT and PET images. Uptake of $^{18}$F-fallypride in the human pancreas is comparable with that in the brain. The degree of specific binding in the pancreas needs to be determined using D2R blocking drugs, such a haloperidol.

3.6 Human PET/CT Imaging with $^{18}$F-Fallypride

Figure 8:
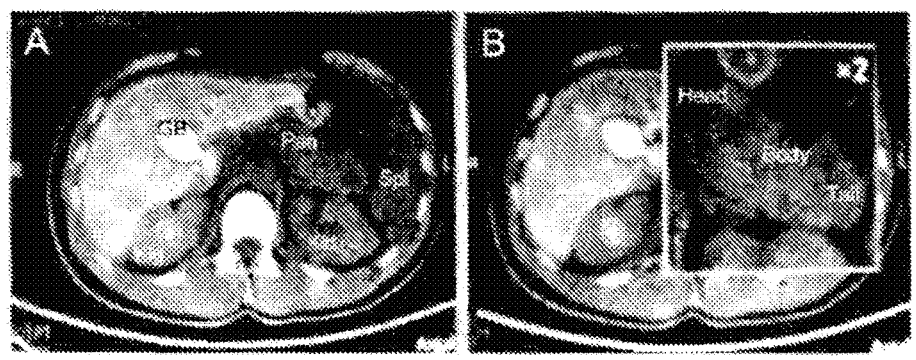
FIG. 8A is an image of human PET/CT section showing $^{18}$F-fallypride binding in various organs (liver, gall bladder (GB), kidneys (Kid), pancreas (Pan), spleen (Spl)).
FIG. 8B is an image of the same human PET/CT section with the pancreas magnified (×2) showing Same slice showing distinct binding of $^{18}$F-fallypride in the head, body and tail regions that are rich in dopamine D2/D3 receptors.

In order to take advantage of the anatomical detail provided by the CT scan, a PET/CT study was done in a normal volunteer. The preliminary PET/CT studies in a normal volunteer using $^{18}$F-fallypride was carried out in a Siemen's PET/CT Biograph scanner. Shown in FIG. 8 are PET/CT images of $^{18}$F-fallypride in the various organs. Gall bladder (GB) and liver exhibited a high degree of activity while kidneys (Kid) exhibited moderate levels of activity. Retention of $^{18}$F-fallypride can be seen in the pancreas (Pan) which was higher than that found in the spleen (Spl) and lungs. FIG. 8B shows a magnified view of the various regions in the pancreas where greater binding of $^{18}$F-fallypride was observed in the head, body and tail regions.

The nonuniform clusters of binding of $^{18}$F-fallypride in the various regions is probably suggestive of the localization of dopamine D2/D3 receptors in the islets. Pancreas (head=1.64; tail=1.86; body=1.7); Liver (right lobe=5.1; left lobe=4.9); Spleen=1.5; Spine-bone marrow=2.8; Stomach=7.5; Gall bladder=123; Kidney=2.2; Lung=1.1, Psoas muscle=0.9; Anterior abdominal muscle=0.6. Table-2 summarizes SUV values of various regions as well as the ratio of pancreas to anterior abdominal muscle and the psoas muscle which are in the field of view of the pancreas.

TABLE 2

Standard uptake values (SUV) of $^{18}$F-fallypride in a normal human Subject using PET/CT.

| Organ | SUV | Ratio Organ/Ant Abd muscle |
|---|---|---|
| Gall bladder | 123 | |
| Liver | 5.0 | |
| Spine | 2.8 | |
| Stomach | 2.2 | |
| Pancreas- Tail | 1.86 | 3.10 |
| Pancreas- Body | 1.7 | 2.83 |
| Pancreas- Head | 1.64 | 2.73 |
| Spleen | 1.5 | |
| Psoas Muscle | 0.9 | |
| Anterior Abdominal Muscle | 0.6 | |

Dopamine D2-like receptors have been found in several other regions in smaller concentrations and are known to contribute to the nigrostriatal, mesolimbic, mesolimbocortical and other dopaminergic pathways. These regions include the thalamus, hypothalamus, amygdala, nucleus accumbens, substantia nigra, frontal cortex, temporal cortex including the hippocampus, colliculi (inferior and superior), pituitary and others. We have successfully used the PET imaging agent $^{18}$F-fallypride to image these receptors in vitro and in vivo in different species (Mukherjee et al., Nucl Med Biol 1995 22:283; Mukherjee et al., Nucl Med Biol 1999 26:519). In human studies $^{18}$F-fallypride distribution of $^{18}$F-fallypride was found to be consistent with the reported distribution of dopamine D2/D3 receptors and the concentrations of the receptors in the various brain regions correlated highly with the known concentrations of the D2 receptors obtained in post-mortem studies. Measurements of receptor concentrations exhibited a test-retest variability mostly within 10% difference. The measured decrease of D2 receptor concentrations in brain regions was attributed to the sensitivity of $^{18}$F-fallypride in detecting changes of D2 receptor concentrations in the brain (Mukherjee et al. Synapse 2002 46:170). In this first investigation, many gross brain structures have been identified that contain D2/D3 receptors that show $^{18}$F-fallypride binding. Detailed neuroanatomical analysis has provided further insights into the localization of D2/D3 receptors in smaller regions such as substantia nigra, hypothalamus, colliculi and other structures (FIG. 6). We have also examined binding of $^{18}$F-fallypride in various sections of the spinal cord (Xue et al., J Nucl Med 2004 45:258P).

Dopamine D2 receptors have also been found in the pancreas of different species. A recent report by Rubi et al., 2005 indicated that the D2 receptors are co-localized alongside the insulin-secreting cells. Development of diagnostic markers for BCM has been underway in order to bring to clinical practice a method to study TIDM and T2DM, we evaluated the capability of $^{18}$F-fallypride to bind and thus identify the density of BCM. Our rat pancreas section clearly indicated that the D2R and insulin-secreting cells are present in the endocrine cells only and not in the exocrine (FIG. 2). This is an important factor in order to study only the insulin-secreting cells.

In rat pancreas sections, $^{18}$F-fallypride bound to regions within the pancreas and this binding was displaced by the D2R blocking drug, haloperidol. This indicated that $^{18}$F-fallypride was indeed binding to a good extent to the D2R. Dopamine, which is a charged molecule, on the other hand did not displace the binding of $^{18}$F-fallypride in the pancreas. This may be because dopamine was unable to permeate the membranes in order to access the $^{18}$F-fallypride-bound D2R. In the ex vivo study, where $^{18}$F-fallypride was injected to anesthetized rats and then were sacrificed at different time intervals, binding to the brain areas was evident as was also binding to the pancreas. The binding in pancreas was greater compared to cerebellum, which is typically used as a reference region.

The streptozotocin-treated diabetes model of Sprague-Dawley indicated loss of insulin-secreting cells, thus a loss in BCM (FIG. 5). Experiments using $^{18}$F-fallypride in pancreas sections of control and treated animals showed a significant decrease in the binding of $^{18}$F-fallypride (Table 1). Similar findings in this diabetes rodent model have been reported using 3H-YM-09151-2 (Eur J Pharmacol. 2007; 557(2-3):99). Thus, D2R serve as a surrogate marker for the loss of insulin-secreting cells.

In human PET studies, $^{18}$F-fallypride localized in the pancreas (FIGS. 7,8). The use of PET/CT allowed the clear delineation of the binding of $^{18}$F-fallypride to different regions within the pancreas. The SUV values for the different organs are shown in Table-2. The ratio between the various regions of the pancreas to abdominal anterior muscle was in the range of 2.7 to 3.1, suggesting that there is sufficient specific $^{18}$F-fallypride binding in the pancreas to detect changes >30%.

The selective, high affinity nature of $^{18}$F-fallypride allows the study of D2R in various brain regions, brain stem, pituitary gland, adrenal glands, spinal cord and pancreas. This capability of $^{18}$F-fallypride may therefore allow the study of the loss (or increase) in BCM as well as changes in the receptor in other organs/regions in the body in various disorders.

Our preliminary PET/CT patient studies show changes in $^{18}$F-fallypride-activity in type 1 diabetic patients compared to normal controls. Various brain regions, pituitary gland, pancreas have been evaluated. The changes in $^{18}$F-fallypride binding has been correlated with levels of C-peptide which is released using glucose administration in these studies.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control.

While the present application has been described in the context of embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is therefore indicated by the appended claims rather than the foregoing description, and all changes that come within the meaning and range of equivalency of the claims are to be embraced within their scope.

What is claimed is:

1. A non-invasive method of monitoring changes in beta cell mass in a subject comprising:
   detecting a first time point level of Dopamine receptor expression in endocrine pancreatic islets in the pancreas of said subject,
   detecting a second time point level of Dopamine receptor expression in endocrine pancreatic islets in the pancreas of said subject, and
   monitoring change in beta cell mass by comparing the first time point level of Dopamine receptor expression with the second time point level of Dopamine receptor expression,
   wherein a reduction of Dopamine receptor expression in endocrine pancreatic islets in the pancreas of said subject is indicative of reduction in beta cell mass, and wherein each of said detecting the first time point level and second time point level comprises an assay comprising the steps of:
   a. administering $^{18}$F-fallypride capable of binding with a high level of specificity to a D2-like receptor into said subject in the presence of haloperidol;
   b. measuring an imaging signal of $^{18}$F-fallypride in the pancreas of said subject in the presence of haloperidol;
   c. administering $^{18}$F-fallypride into said subject in the absence of haloperidol;
   d. measuring an imaging signal of $^{18}$F-fallypride in the pancreas of said subject in the absence of haloperidol;
   e. detecting the level of Dopamine receptor expression in endocrine pancreatic islets by subtracting the imaging signal in the presence of haloperidol from the imaging signal in the absence of haloperidol;
   and wherein the reduction in beta cell mass is predictive of being at risk or predisposed to developing clinical symptoms of diabetes in the subject.

2. The non-invasive method of claim 1, wherein said imaging signals of said $^{18}$F-fallypride is measured by positron emission tomography (PET) or positron emission tomography-computerized tomography (PET/CT) or positron emission tomography-magnetic resonance imaging (PET/MRI).

3. The method of claim 1, wherein said subject is at preclinical stage of diabetes.

4. The method of claim 3, wherein said diabetes is Type 1 or Type II diabetes.

5. The method of claim 1, wherein said subject is at clinical stage of diabetes.

6. The method of claim 5, wherein said diabetes is Type I or Type II diabetes.

7. The method of claim 1 wherein said subject is at preclinical stage or clinical stage of a diabetes-related metabolic syndrome.

8. The method of claim 1 wherein the administrations of $^{18}$F-fallypride are administered with glucose.

9. The method of claim 1 wherein an oral glucose test is conducted simultaneously.

10. The non-invasive method of claim 1, wherein said Dopamine receptor is D2 receptor.

* * * * *